United States Patent [19]

Levin

[11] Patent Number: 5,141,866
[45] Date of Patent: * Aug. 25, 1992

[54] PROCESS FOR PLANT TISSUE CULTURE PROPAGATION

[76] Inventor: Robert Levin, c/o Plant Biotech Industries Ltd., Mobile Post Ashrat, 25201, Israel

[*] Notice: The portion of the term of this patent subsequent to Aug. 8, 2006 has been disclaimed.

[21] Appl. No.: 210,569

[22] Filed: Jun. 22, 1988

Related U.S. Application Data

[63] Continuation-in-part of Ser. No. 203,640, Jun. 3, 1988, Pat. No. 4,855,236, which is a continuation of Ser. No. 634,112, Jul. 24, 1984, abandoned, and a continuation-in-part of Ser. No. 634,772, Jul. 26, 1984, abandoned.

[30] Foreign Application Priority Data

Jul. 26, 1983 [DE] Fed. Rep. of Germany ........... 69332
Jul. 26, 1983 [DE] Fed. Rep. of Germany ........... 69333

[51] Int. Cl.⁵ .................. C12N 5/00; C12N 5/02; C12M 3/00; C12M 3/02; C12M 1/00; C12M 1/12
[52] U.S. Cl. .................. 435/240.45; 435/240.46; 435/284; 435/286; 435/287; 435/311
[58] Field of Search ............... 435/30, 240.45, 240.46, 435/240.48, 240.49, 240.5, 240.51, 261, 287, 311, 803, 284, 285, 286

[56] References Cited

U.S. PATENT DOCUMENTS 4,855,236 8/1989 Levin ........................... 435/240.45

Primary Examiner—David T. Fox

[57] ABSTRACT

The invention provides a process for at least semi-automated plant tissue culture propagation comprising: providing plant tissue culture containing a large number of densely packed meristematic areas, automatically separating and thinning the tissue into small clusters of meristematic tissues, bulk transporting the separated tissue aseptically to a separating apparatus wherein the tissue is washed and propagules of substantially uniform size and substantially free of phytotoxic cell debris are obtained, aseptically transporting the propagules to a culture vessel and distributing the propagules on the surface of a culture medium. The culture medium is contained in a plant tissue culture vessel provided with a substantially flat fine screening element elevated above the inner bottom surface of the vessel, the vessel being sterilizable, substantially sealable and adapted for growing plant tissue cultures supported on the surface of the screening element in optimal contact with culture medium filling the vessel to the level of the screening element, the screening element being sized to permit the passage of the culture medium therethrough while retaining the tissue culture on the surface thereof.

7 Claims, 3 Drawing Sheets

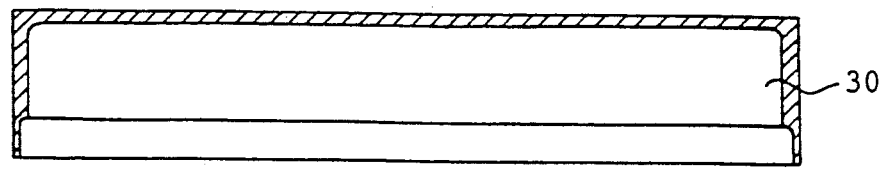
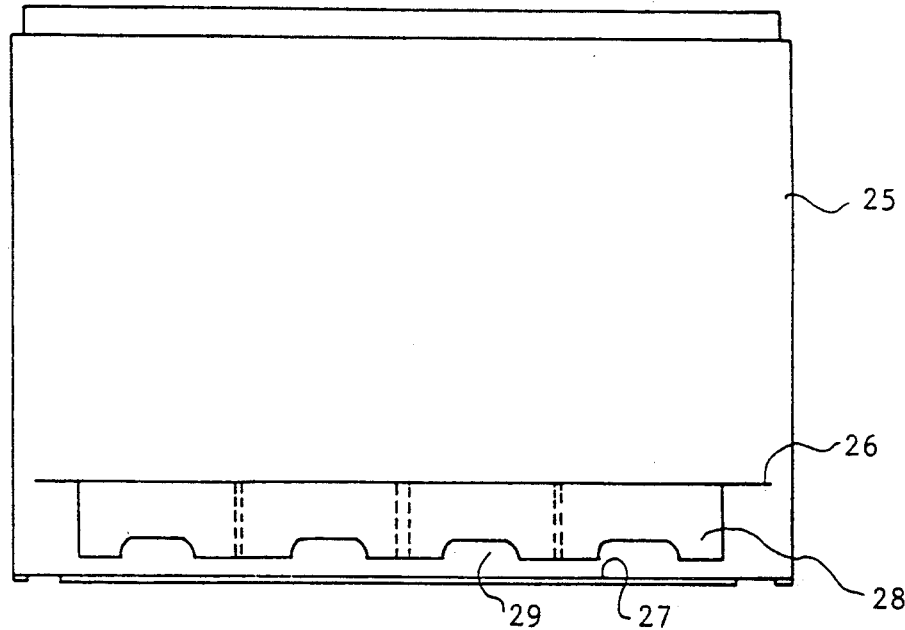
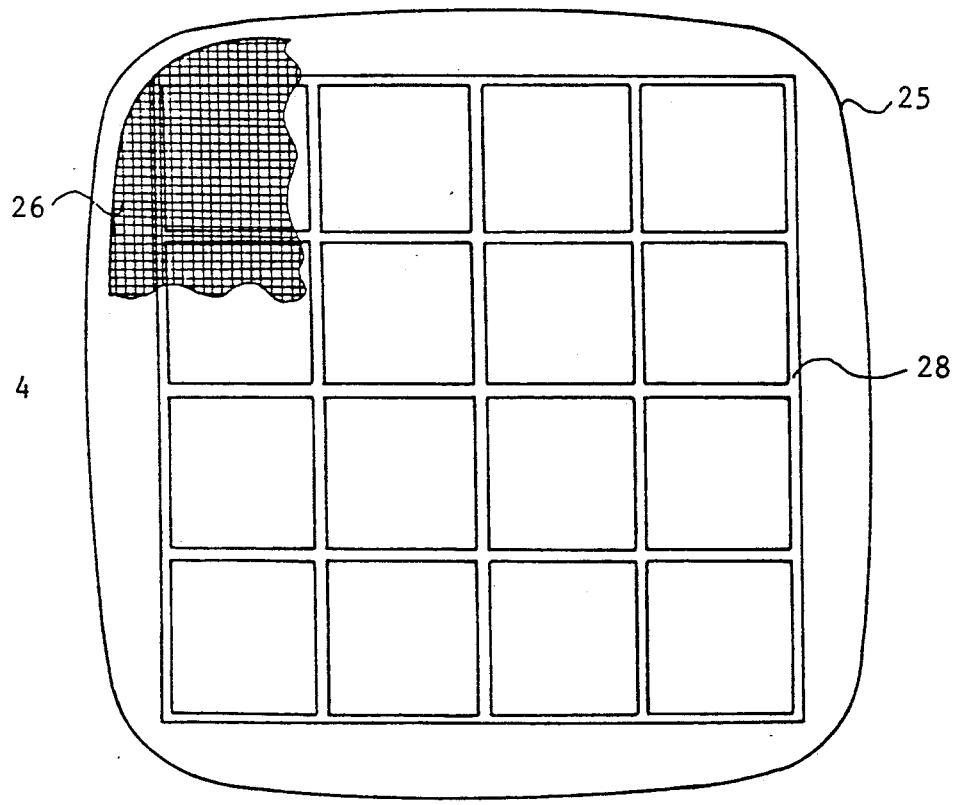

PROCESS FOR PLANT TISSUE CULTURE PROPAGATION

This application is a continuation-in-part of Ser. No. 07/203,640, filed Jun. 3, 1988, now U.S. Pat. No. 4,855,236 granted Aug. 8, 1989, which is a continuation of Ser. No. 06/634,112, filed Jul. 24, 1984, now abandoned. This application is also a continuation-in-part of Ser. No. 06/634,772, filed Jul. 26, 1984, now abandoned.

The present invention relates to a process for plant tissue culture propagation.

More particularly the present invention relates to a process involving the sterile, at least semi-automatic separation of clumps of buds or shoots produced on an "In Vitro" multiplication medium and their sterile transfer to a growth or multiplication medium.

The conventional procedure for plant tissue culture propagation is widely practiced and extensively reviewed in the literature. For example, current practices are described by P. F. Wetherell, "In Vitro Propagation" (Avery 1982); B. V. Conger, Ed; "Cloning Agricultural Plants via In Vitro Techniques". (CRC Press, 1981); T. A. Thorpe "Plant Tissue Culture-Methods and Applications in Agriculture" (Academic Press, 1981). Simply viewed, "in Vitro" propagation consists of aseptically removing a portion of a plant and placing it on a nutrient medium which causes growth and/or proliferation to occur. More particularly, plant tissue culture can be divided into a sequence of three major stages. The objective of the first stage is the initiation of rapidly developing aseptic culture. This culture can be initiated from a number of plant organs.

Typically, explants are surface disinfected and then handled under sterile conditions. After disinfection, explants are rinsed several times with sterile distilled water and cut into desired segments with sterile instruments. The explant is then placed in a culture vessel in contact with the media and the vessel is placed in a culture room in which light quantity, photoperiod, and temperature are controlled.

After approximately six to eight weeks in the culture room the developed explant material is used for the initiation of the multiplication stage of 'In Vitro' propagation. Here the developed explant is aseptically removed from its vessel and trimmed and divided if necessary. The tissue is then placed in a cultural vessel on a medium with the appropriate hormone composition and balance to induce multiplication—and returned to the culture room. After about another six to eight weeks in the culture room on a multiplication medium the tissue is aseptically removed from its vessel, divided, transferred to fresh medium and returned to the culture room. This transfer is either to a growth medium which is formulated to induce development of shoots, with or without roots, that will withstand the transition to the greenhouse environment or to a multiplication medium once again for further propagation The ability to repeatedly recycle tissue culture through the multiplication stage (Stage II) accounts for the rapid increases which are one of the main advantages of 'In Vitro' propagation. This procedure, however, is a very labor intensive activity, and it has been estimated that as much as 60–65 per cent of the cost of producing plants 'In Vitro' can be attributed to wages, salaries and associated costs (W. C. Anderson, G. W. Meagher and A. G. Nelson, Cost of Propagating Broccoli Plants through Tissue Culture Hortscience 12: 543–544, 1972); (A. Donnan, Jr., S. E. Davidson and C. L. Williams, Establishment of Tissue Grown Plants in the Greenhouse Environment. Proc. Fla. State, Hort. Soc. 91: 235–237, 1978). Consequently, there have been many attempts to reduce labor related expenses.

One such attempt was a study by Ron C. Cooke, Homogenization as an Aid in Tissue Culture Propagation of Platycerium and Davallia Hort-Science 14: 21–22, 1979, where manual dissection and transfer of the multiplication stage of fern tissue culture was replaced by aseptic homogenization and volumetric transfers to fresh media.

These findings initially raised the possibility that some form of blending or chopping procedure could provide the basis of a partially automated 'Vitro' propagation scheme, however, tests or studies in our laboratory indicated that Cooke's procedure would not be adequate for this purpose for the following reasons:

I. Contamination could easily be introduced into the homogenate.
II. For some species (Ferns, Ficus, Lilium and Philodendron were examined) a homogenate which was concentrated enough to provide dense growth in the culture vessel was too viscous to dispense volumetrically. Removing this homogenate with a spatula was neither a sufficiently automatic procedure nor a sufficiently sterile one. Dilution of this homogenate with media, as in Cooke's (1978) study, results in a large portion of the plant material settling to the bottom of the culture vessel, where it fails to grow. Dilution of the homogenate with sterile water and inoculating the surface of solid agar medium (another of Cooke's procedures) resulted in sparse growth in the culture vessel for the species we examined.
III. Homogenization in the species examined does not provide a sufficiently uniform inoculum which in turn results in a lack of uniform growth in the culture vessel.
IV. Homogenization can result in the release of phytotoxid compounds.

After further research there was developed according to the present invention a process for at least semiautomated, and eventually, completely automated, plant tissue culture propagation comprising: providing plant tissue culture containing a large number of densely packed meristematic areas, automatically separating and and thinning said tissue into small clusters of meristematic tissues, bulk transporting said separated tissue aseptically to a separating apparatus wherein said tissue is washed and propagules of substantially uniform size and substantially free of phytotoxic cell debris are obtained, aseptically transporting said propagules to a culture vessel and distributing said propagules on the surface of a culture medium.

Prefeably said separated tissue is aseptically bulk transported to a sieving apparatus and sieved and washed to obtain propagules of substantially uniform size and substantially free of phytotoxic cell debris and in especially preferred embodiments of the invention, as will be described hereinafter said sieved propagules are aseptically transported to a culture vessel provided with a screening element sized to retain propagules on the surface thereof and filled with culture medium to a level wherein the surface of said medium contacts said propagules, whereby said propagules are supported on said screening element with optimal contact with the culture medium.

It will thus be realized that the present invention solves the above mentioned problems and therefore provides a substantially automated general method of separation of plant propagules derived from 'In Vitro' multiplication and their transfer to a growth or multiplication medium. The resultant reduction in labor costs can significantly reduce the cost of crops currently propagated 'In Vitro'. The invention will also allow tissue culture propagation of crops which are currently less expensive to propagate by conventional methods. Finally, for some species, the invention can allow plant breeders to economically undertake tasks such as 'In Vitro' propagation of parent lines, hybrids etc. and 'In Vitro' selection at the whole plant level, which are prohibitively expensive by conventional 'In Vitro' propagation methods.

Briefly, in accordance with the invention, partial automation of plant tissue culture propagation is achieved by performing the following operations under sterile conditions. Multiplication stage culture is homogenized, washed with distilled water and sieved to obtained propagules of uniform size. The propagules are then mixed with medium and dispensed to culture vessels in such a manner that the plant material lies on an even layer on top of a medium base. This is accomplished by dispensing the plant/medium mixture to culture vessels fitted with screen inserts one cm above the bottom of the vessel. The screens allow the medium to pass but hold the propagules. The mixture is added until the level of the medium reaches the level of the screens so that an even layer of plant material lies on top of a medium base.

This invention is based on the recognition of several points. One of these points is that a homogenization procedure could be applicable for most species which during the multiplication stage could be induced to form a culture consisting of dense clumps of meristematic tissue capable of developing into shoots, as is the case with ferns. Another point is that the problems associated with Cooke's homogenization procedure, as noted above, are soluble by diluting the homogenate, under sterile conditions, to allow volumetric dispensing and treatment of the homogenate and then reconstituting a concentrated inoculum on the surface of the medium in the vessel.

Recognition of these points is central to the invention of a process of partial automation of plant tissue culture production. However, these realizations occured only after extensive experimentation. It was first necessary to determine whether species such as Lilium, Ficus and Philodendron could be efficiently separated by a homogenization procedure. It was found that if these varieties were homogenized in sterile water, the homogenate strained to remove the water, and the plant material spread over the surface of solidified medium then dense growth could be obtained. Further, if the homogenate was rinsed to remove phytotoxic cell debris prior to being strained, then the rate of multiplication was not less than that obtained by conventional tissue culture.

It was also found, however, that a homogenate concentrated enough to produce dense growth was too viscous for volumetric dispensing and that contamination was still a major problem.

In trying to deal with the problem of contamination it was found that the source of this contamination was both latent contamination of the plant material and working with open vessels even under standard aseptic conditions. Further, this contamination could not be effectively controlled by mycostatic and bacteriostatic compounds. However, culture indexing the multiplication stock and blending the plant material in a closed blender and transporting the homogenate to culture vessels by volumetric dispensing through a peristaltic pump, allowed successful propagation of ferns such as Platycerium.

Nevertheless, the problem remained as to how to deal with the situation where the homogenate necessary for dense growth was too viscous for volumetric dispensing.

Said problem was solved by bulk transporting the separated tissue aseptically to a separating apparatus wherein said tissue is washed and propagules of substantially uniform size and substantially free of phytotoxic cell debris are obtained and then aseptically transporting said propagules to a culture vessel and distributing said propagules on the surface of a culture medium.

In this manner all of the above mentioned problems were solved and an at least semi-automated commercial process for plant tissue propagation developed.

The advantage of such a process is that it fills a long felt need and significantly lowers the production costs of commercial propagators and breeders. It is estimated that the invention can reduce by 75 percent the cost of recycling multiplication stage culture and production of plantlets which can be transferred to the greenhouse.

After further research and development it was also found that if the culture vessel were fitted with a screen several cms above the base of the vessel, then a mixture of plant tissue and medium could be dispensed in such a way that a viscous layer of plant material would lie on top of and in good contact with a medium base. This would allow homogenate to be volumetrically dispensed in a manner that would allow good growth and development. This method was successful and therefore is incorporated in preferred embodiments of the invention.

Another advantage of this preferred embodiment is that it allows for inexpensive large scale 'In Vitro' screening of whole plants for resistance to environmental stress. That is, since the plantlets are grown on a screen the plants can be transferred in bulk to a medium which contains the agent to be selected against (e.g., a fungal wilt), or more simply, the liquid medium under the screen can easily be changed and the agent to be selected against be introduced with the new medium.

In accordance with one aspect of the invention, sterile, culture indexed, multiplication stage culture, comprised of a compact mass of meristematic tissue is introduced to a sterile blender and blended for several seconds. In accordance with another aspect of the invention, the homogenate is aseptically diluted with distilled water, and transferred by peristaltic pump to an aseptic sieving process. This process consists of passing the diluted homogenate through a coarse sieve to trap the large pieces of tissue which are ultimately blended again. The material which passes through the coarse sieve reaches a fine sieve which traps the propagules and allows cell debris and tissue pieces too small to regenerate to pass through. The propagules trapped by the fine sieve are aseptically washed by passing a stream of distilled water over the sieve, and then resuspended by adding a fixed volume of distilled water and stirring. This suspension is then aseptically transferred by peristaltic pump to a holding tank, containing either concentrated liquid medium or concentrated agar based medium, constantly stirred and maintained at 37° C. to prevent solidifcation. The medium can be one which is formulated either to promote multiplication or to support the growth of shoots which can subsequently be transferred to the greenhouse.

The addition of the fixed volume of water in the plant homogenate suspension is calculated to bring the medium concentration in the holding tank to normal strength. After the propagules are thoroughly mixed in the tank, the plant/medium mixture is aseptically dispensed by peristaltic pump into culture vessels fitted with fine mesh screen inserts. These inserts rest on a support above the bottom of the vessel which allows the medium to pass through the screen while holding the propagules. The mixture is evenly dispensed in the culture vessel and the vessel filled until the medium reaches the level of the screen. This process results in a thin dense layer of plant material in good contact with a medium base.

After the vessels are filled they are transferred to a standard culture room with controlled light quality, photoperiod and temperature. After six to eight weeks in the culture room, multiplication stage culture is recycled through the homogenization process. However, prior to being blended, the culture is transferred for several weeks to a medium which will easily show contamination. This is to allow the medium to be tested for sterility and thus prevent the introduction of contamination into the holding tank which would cause all the culture produced from the tank to be discarded. Culture on a growth promoting medium, after approximately six to eight weeks in the culture room is simply transferred to the greenhouse.

Broadly, the process of the present invention comprises the following procedural steps:
I. Automatically separating and thinning plant tissue culture containing a large number of densely packed merstematic areas into small clusters of meristematic tissue by homogenization, chopping, or some other procedure;
II. Bulk aseptic transportation of this separated tissue to an apparatus where the tissue is washed and propagules of substantially uniform size and substantially free of phytotoxic cell debris are obtained;
III. Aseptic transportation of these propagules to a culture vessel and distribution of the propagules evenly on the surface of a culture medium.

More specifically the preferred process of the present invention comprises:
a) providing plant tissue culture containing densely packed multi-meristematic tissue;
b) automatically separating and thinning said tissue into small clusters of meristematic tissue;
c) bulk transporting said separated tissue aseptically to a sieving apparatus wherein said separated tissue is sieved and washed to obtain propagules of a predetermined size range and substantially free of phytotoxic cell debris;
d) aseptically combining said sieved propagules with a liquid culture medium;
e) dispensing said mixture into culture vessels, said vessels being provided with a screening element sized to enable the culture medium to pass therethrough while retaining the propagules on the surface thereof; and
f) filling said vessels to a level wherein the surface of the said medium contacts said propagules, whereby said propagules are supported on said screening element with optimal contact with the culture medium.

Preferably said small clusters of meristematic tissue from step b) are diluted with sterile aqueous medium to facilitate volumetric transportation and are then pumped to said sieving apparatus and said sieved and washed propagules of step c) are diluted with a sterile aqueous medium to facilitate volumetric transportation and are then pumped to a holding tank.

In one preferred embodiment of the present process said propagules in the holding tank are aseptically combined with a liquid culture medium to form a uniform mixture, said culture medium preferably being an agar-based medium maintained in a liquid state by being held at a temperature of 37° C., and then said propagule/medium mixture is volumetrically dispensed to culture vessels by being pumped to said vessels.

In the process of the present invention both the initiation of tissue culture and the transfer to the multiplication stage are performed using conventional methods which were briefly described earlier. It should be noted that the medium for this culture may be liquid or solid and the procedure either a stationary or shake culture, however all multiplication stage culture is preferably placed on a liquid medium for several weeks prior to separation and thinning to allow the medium to be tested for contamination.

Said separation and thinning is preferably carried by use of a blender or homogenizer having rotating blades which in a period of about 4-9 seconds separate and thin the tissue into small clusters of meristematic tissues. This preferred procedure will be referred to hereinafter as homogenization and the liquid exiting therefrom as a homogenate even though the homogenizer or blender is intentionally stopped before a true homogenate is produced as explained and described hereinafter.

Thus in summary, the process preferably provides for at least partial automation of plant tissue culture propagation by carrying out the following steps under aseptic conditions:
a) Multiplication stage plant tissue culture consisting of masses of meristematic tissue is homogenized;
b) The homogenate is diluted and volumetrically transferred to a sieving apparatus;
c) The homogenate is washed and sieved to obtain propagules of a predetermined size range;
d) The propagules are diluted and transferred to a holding tank containing medium; and
e) The propagule/medium mixture is dispensed to culture vessels fitted with screens so that the plant material will form a layer on the screens over the medium base.

As indicated, several weeks before homogenization, the multiplication stage culture is preferably tested for possible contamination as described hereinafter.

Flasks of multiplication stage culture are brought to the sterile room, opened on a laminar flow clean bench, and approximately 3 ml of liquid medium is aseptically withdrawn by pipette. Aliquots of 0.5 ml of this medium are then added to 5 ml of sterile test medium. Three separate index media are used: yeast extract+dextrose (10 g/liter) broth; Sabouraud liquid and AC broth; and trypticase Soy broth, and each multiplication stage flask is tested in duplicate with each of these media. After the index medium is incubated for two weeks at 27° C. it is examined. Culture flasks which are shown to be contaminated are discarded and the rest of the flasks are homogenized.

Prior to the homogenization procedure, all equipment which comes in contact with plant tissue is sterilized by autoclaving at 121° C. for 20 minutes. The equipment is sterilized in containers open to the steam, which are closed as soon as the autoclave is opened. These sealed containers are brought to the sterile room and opened only in a laminar flow clean bench. An exception to this procedure is the holding tank which is self sterilizing. The personnel, who wear sterile gowns and gloves throughout the entire procedure, aseptically connect the tubing to the various pieces of equipment under a laminar flow clean hood.

The invention will now be described in connection with certain preferred embodiments with reference to the following illustrative figures and in the following example, so that it may be more fully understood. It is stressed, however, that the particulars shown and described are by way of example and for purposes of illustrative discussion only and are presented in the cause of providing what is believed to be the most useful and readily understood description of the principles and conceptual aspects of the invention. In this regard no attempt is made to show structural details of apparatus utilizable in the claimed process in more detail than is necessary for a fundamental understanding of the invention, the description taken with the drawings making apparent to those skilled in the art how the several forms of the invention may be embodied in practice.

In the drawings:

FIG. 3 is a cross section of a culture vessel employed in the invention;

FIG. 4 is a top view of the culture vessel showing a pallet and only a portion of a screening element positioned thereon; and FIG. 5 is a cross section of the cover of the vessel.

The homogenization process begins with the filling of the holding tank with double strength medium. This holding tank is a commercially available EGMO ES-8 8 liter capacity media sterilizer-dispenser which has been modified to allow the dispensing of a plant/medium mixture. These modifications consist of:

A) Enlarging the outlet port from 9.5 mm (inside diameter) to 12 mm (inside diameter).
B) Replacing the original outlet valve with a pneumatically operated ball valve,
C) Making two special arrangements to ensure sterility in the valve,
  1) allowing the outlet valve to remain open during sterilization, the outlet itself being closed with a screw cap.
  2) attaching a 50 W heating element to the valve to ensure it can reach sterilization temperature.
D) The agitator was extended to within several mm of the base of the chamber to ensure good mixing with small volumes.

Once filled, the holding tank sterilization cycle is started. The media is heated to 121° C., held at this temperature for 20 minutes, cooled to 37° C. and aseptically maintained at this temperature. After completion of this cycle, which takes about 75 minutes, the holding tank can be aseptically connected to the rest of the apparatus.

Figure 1:
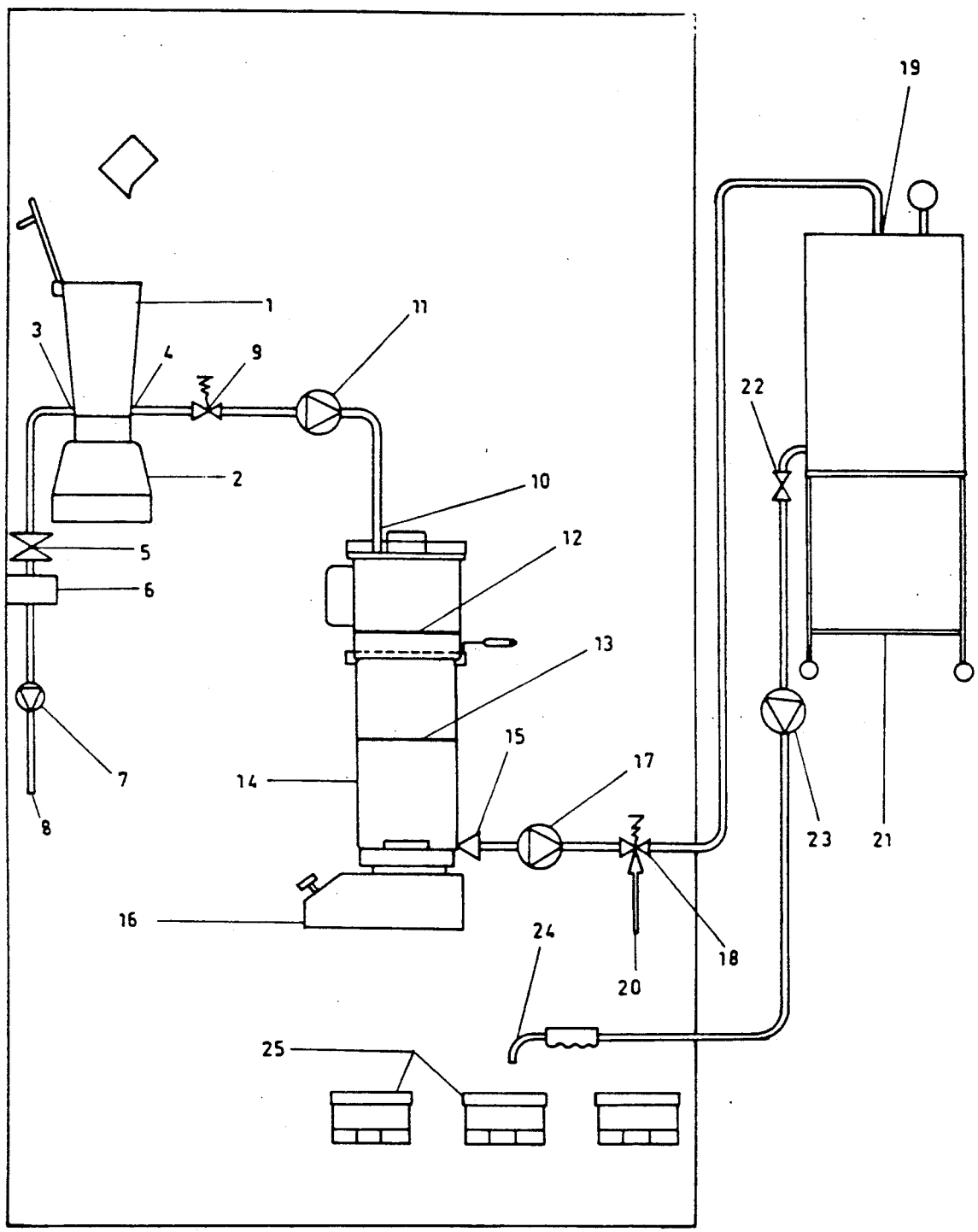
FIG. 1 is a flow diagram illustrating the process of the invention.

The manner in which the various pieces of apparatus are connected to one another can be seen in FIG. 1. On the clean bench a Waring sterile dispensal blender (1), modified for use by enlarging the outlet from 9.5 mm inside diameter to 12 mm inside diameter, is removed from its container and set on its base (2). The blender is autoclaved with silicone tubing attached to the inlet port (3) and the outlet port (4) together with the equipment connected to the other side of the tubing. Connected to the inlet port through the inlet valve (5) is an in line 0.22 micron filter (6). This filter is later connected through a Cole-Parmer Masterflex peristaltic pump No. 7534-10 fitted with head No. 7018-20(7) to a 45 liter carboy of distilled water (8), thus providing a source of sterile water. The tubing from the outlet port is connected to the outlet valve (9), which is in turn connected to the inlet of the cover of the sieving apparatus (10). This tubing is later passed through a Cole-Parmer Masterflex peristaltic pump No. K7549-19 fitted with head No. 7019 (11).

Figure 2:
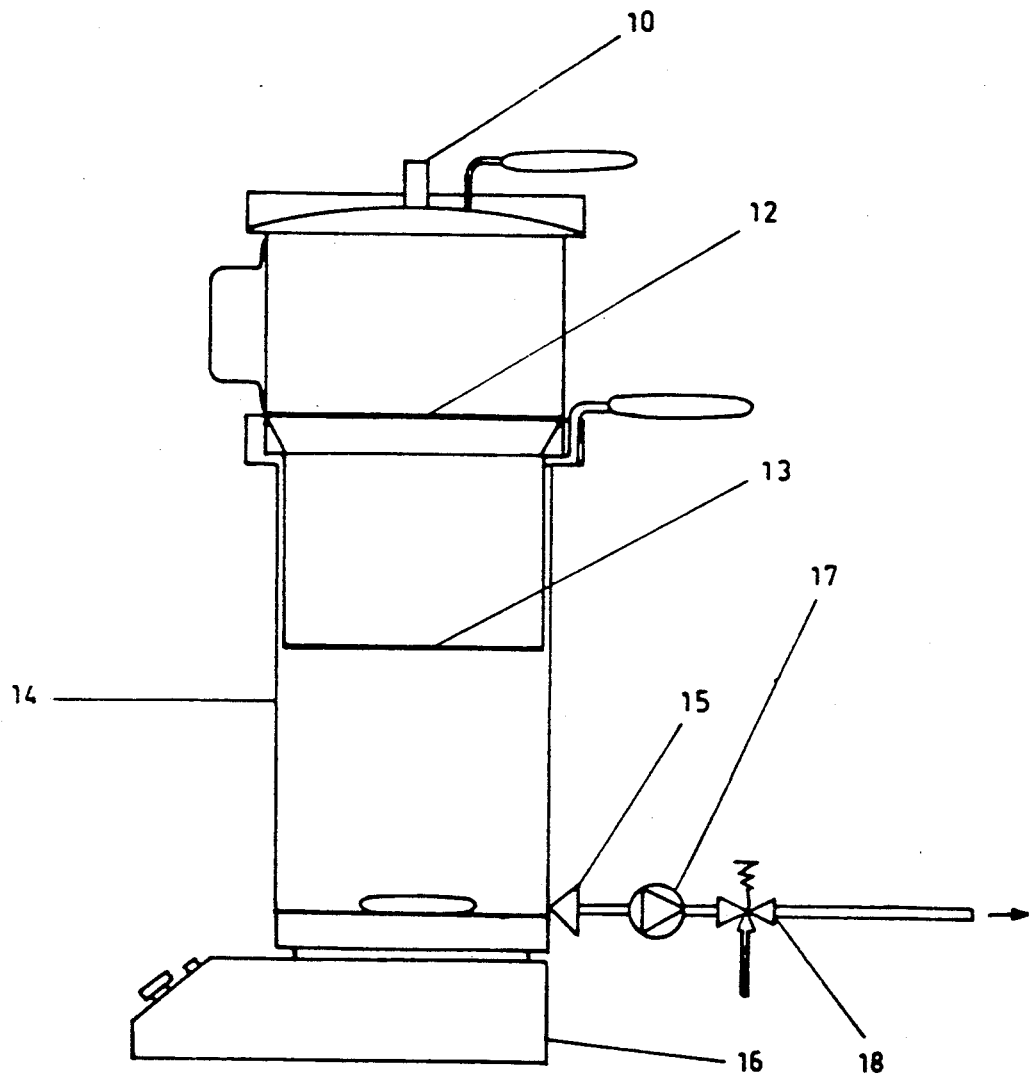
FIG. 2 is a side view of the sieving apparatus.

The construction of the sieving apparatus can be clearly seen in FIG. 2. Briefly, this apparatus consists of a stainless steel coarse sieve (12), which sits over a stainless steel fine sieve (13). The fine sieve rests in a stainless steel container from which it can be removed (14). This container is constructed so that it has a closable outflow valve (15).

The sieving apparatus is aseptically removed from its container and assembled next to the blender resting on a magnetic stirrer (16). The container in which the fine sieve rests is autoclaved with a magnetic stirring bar inside and with the outflow valve connected to silicone tubing. The other side of the tubing is connected thorough a Cole-Parmer masterflex peristaltic pump No. K7549-19 fitted with head No.7019 (17) to a two-way valve (18). One leg of this two-way valve is connected to tubing which will be attached to the intake port of the holding tank (19). The other leg of this valve is connected to tubing that will carry the rinse water from the sieving apparatus to an empty carboy (20). All of the tubing including the 2-way valve is autoclaved with the sieving apparatus.

After the apparatus is assembled on the sterile table, the sterile connections to the holding tank are made. The holding tank sits on a cart (21) which allows it to be rolled into the laminar air flow of the clean bench. Here the tubing connection from the sieving apparatus is attached to the intake port of the holding apparatus. A sterile silicone tube is also attached to the valve of the dispensing port (22). This tube passes through a Cole-Parmer Masterflex peristaltic pump No. 7534-10 fitted with head No. 7018-20 (23) and returns to the sterile table. The dispensing end of this tube (24) remains on the table until the vessels (25) are filled. Once all the connections are made the holding tank is removed from the table and the actual homogenization procedure can be initiated.

The procedure begins with the pouring of sterile multiplication stage culture into the blender. Usually about 160 grams of plant material and about 400 ml of liquid are introduced into the blender, although this may vary somewhat. The plant material is not directly weighed but rather the experienced technician judges the weight of the culture by its volume. Generally the medium in the flask does not provide enough liquid and so sterile water is added to the blender and again, the amount of water necessary is estimated. Next, the blender is tightly closed and the plant material blended for somewhere between 3 to 9 seconds at low speed. The duration of blending will also vary with a number of conditions, with the optimal time being determined by preliminary studies. It should be noted that blending for too long a period results in excessive tissue changes and poor growth. Blending for too short a period does not divide the culture. After blending the inflow and outflow valves are opened, and the peristaltic pumps which bring sterile water into the blender and dilute homogenate out of the blender are started. The flow of these pumps are balanced so that inflow volume equals that of the outflow. The flow is continued until the blender is emptied of plant material. The inflow peristaltic pump is then shut, the blender drained and the outflow pump shut. Next, the inflow and outflow valves are shut, the blender opened and the process repeated. The blending continues until enough plant material has been processed to fill the holding tank. The specific amount of plant material used will, of course, vary according to a number of factors including species, desired density in the culture vessel etc.

From the blender the dilute homogenate is pumped to the sieving apparatus. The coarse sieve catches clumps of plant tissue but allows passage of most of the homogenate. From time to time the contents of the coarse filter are returned to the blender. This is accomplished by inverting the filter over a sterile stainless steel beaker and rinsing the plant material into the beaker with sterile distilled water from the outflow blender. The coarse sieve is then returned to its usual position and the process continued.

The homogenate reaching the fine sieve contains a mixture of propagation material, cell debris and pieces of plant tissue too small to regenerate quickly into plants. The fine sieve retains the plant propagules while cell debris and very small pieces of tissue pass into the container which holds the sieve. The exit valve of this container is then opened, the peristaltic pump started and flow through the two-way valve directed to the carboy holding the rinse water. The pinch clamp leading to the carboy is also opened and the rinse water begins to flow to the carboy (the purpose of this pinch clamp is to prevent a back flow of air from contaminating the apparatus at times when water is not flowing).

After the blending has been completed, water continues to run through the system until the rinse water runs clear. The pinch clamp is then closed as is the exit valve of the sieve container. Next, four liters of sterile distilled water is run into the container. The magnetic stirrer is then started and the fine sieve is manually inverted in the container thus resuspending the propagates in the water in the container. The flow from the container is now directed to the intake port of the holding tank. The exit valve of the container is opened and the suspension pumped into the holding tank slowly so as not to lower the temperature of the medium. When the suspension has been transferred and mixed with the medium, bringing that medium concentration to normal strength, the plant/medium mixture can be dispensed into the culture vessels.

The culture vessels including the screen inserts and supports are autoclaved in the same manner as the apparatus and brought to the laminar flow clean bench in sealed containers. The culture vessels are 100 cm$^2$ polycarbonate containers fitted with a one cm high polycarbonate support on which rests a 500 micron mesh opening nylon screen. The culture vessels are aseptically removed from their container on the clean bench, opened and filled one by one. In the filling operation the plant/medium mixture is slowly and evenly dispensed by peristaltic pump over the screen. The propagules are held by the screen while the media passes through. Dispensing continues until the level of the medium reaches the level of the screen which produces a thin layer of plant material resting in good contact with medium base. When the holding tank is emptied the dispensing stage is completed. The holding tank is returned to the clean bench, the connections to the intake and dispensing ports are aseptically disconnected and the tank removed for cleaning and reuse. A new holding tank containing double strength medium at 37° C. is brought to the clean bench, aseptically connected to the apparatus and the proceeding process repeated.

Filled vessels are sealed with parafilm and transferred to a culture room. Although the optimal growth conditions will vary depending on a number of factors, in general the environmental conditions after homogenization are the same as those required by conventional tissue culture.

After about six to eight weeks in the culture room, culture on a growth medium can be transferred to the greenhouse and multiplication stage culture can be recycled through the homogenization process. The first step in subculturing this multiplication stage material through the use of the homogenization process is to aseptically transfer this material to a liquid medium if it is not already on one. This is accomplished by bringing the culture vessel to the laminar flow clean bench in the sterile room. Here each vessel is opened and the screen to which the culture adheres is removed. The culture is separated from the screen with a sterile spatula and placed in a beaker of sterile water. The water is agitated by stirring on a magnetic stirrer to wash the agar from the plants and the mixture poured through a coarse stainless steel sieve. The sieve is then inverted over a stainless steel beaker and liquid multiplication stage medium is poured through the sieve to rinse free any culture still clinging to it. The medium with the tissue suspended in it is then poured into a sterile flask, stoppered and returned to the culture room. In the culture room the flask may sit on a shelf, on an orbital shaker or on a reciprocal shaker depending on which conditions provide the best results for the particular culture. After several weeks in the culture room, the liquid medium is checked for sterility with the procedure described above. If the culture is not found to be contaminated it can once again enter the homogenization process. Ideally, the horticultural tests for phenotypic stability should take place before the initiation of large scale commercial production. Thus at least several hundred plantlets derived from an initial culture and a number of subsequent subcultures must be adapted to greenhouse conditions, grown to maturity and examined for the phenotypic characteristics of economic importance to the variety being propagated. In order for the homogenization process to be useful for commercial propagation an unacceptable level of phenotypic off-types should not occur in the initial culture or in the first few subcultures. Should an unacceptable level of off-types appear in the first few subcultures, then an alteration in some of the 'In Vitro' procedures such as a change in the explant material used or the hormone content of the multiplication medium may rectify the situation. However, if the phenotypic variability cannot be reduced to acceptable levels then the particular variety or clone of that variety is unsuitable for propagation by homogenization procedure. The appearance of an unacceptable level of phenotypic offtypes after a number of subcultures marks the point at which subculturing must be discontinued and the culture reinitiated from explant material.

EXAMPLE 1

Tissue culture of Philodendron Burgundy was initiated and subsequently subcultured and propagated for eight generations using the process described above. Two hundred plantlets from the initial culture and 2,500 plantlets from each subculture were transferred to the greenhouse and grown for six months. None of these plants showed unacceptable phenotypic variability and all were marketed.

Maintenance of Stock Plants

Explant tissue was derived from 500 one year old Philodendron Burgundy mother plants. These plants had been maintained for at least six months under conditions which would facilitate obtaining non-contaminated explants. More particularly these plants were housed in individual pots in a greenhouse with a relatively low humidity (approx. 70%) and a relatively high temperature (approx. 25° C.) These plants received water only at the base and were prophylactically sprayed with the fungicides Benlate (1 gm/liter) and Captan (2 gm/liter) once a week and the insecticide Azadrin (3 ml/liter) once every ten days.

Initiation of 'In Vitro' Culture

Several days after the plants were sprayed with the fungicides, 600 shoot tips (4-5 cm long) were removed from the mother plants and brought to the laboratory. The explants were surface sterilized by immersion first in 1.0% Proceptil for 30 minutes, next in a solution of 0.2% Captan and 0.1% Benlate for 30 minutes and finally in a 1.0% Sodium Hypochlorite solution for 20 minutes. The explants were then brought to the sterile room, placed on a laminar flow clean bench and rinsed three times in sterile distilled water. The shoot tips were than aseptically trimmed down to 3-5 mm in length and placed in test tubes, vertically, on 10 ml of initiation stage medium. This medium consisted of MS salts (Murashige and F. Skoog—A Revised Medium for Rapid Growth and Bioassy with Tobacco Tissue Culture Physiol. Plant. 15: 473-497, 1962), myo-inositol 100 mg/liter, glycine 2 mg/liter, nicotinic acid 5 mg/liter, pyridoxine 5 mg/liter, thiamine 10 mg/liter, BA 10 mg/liter, sucrose 30 grams/liter, Difco Bacto-Agar 10 grams/liter and was adjusted to pH 5.7 before autoclaving. The test tubes were then sealed with Kimble PM (permeable membrane) caps and placed in the culture room. The culture room was maintained at 26° C. ±1 under 4,000 lux cool white fluorescent illumination and a 16 hour photoperiod. The culture was inspected weekly and contaminated test tubes were removed and discarded.

Initiation of Multiplication Stage

After about six weeks in the culture room the developed explants were returned to the sterile room for transfer. Of the original 600 explants, 300 had developed and were not visibly contaminated. These explants were aseptically trimmed, separated and placed in test tubes with fresh multiplication stage medium, the composition of which was the same as the initiation medium. The test tubes were again sealed and returned to the culture room for another six to eight weeks. When the multiplication stage culture was ready for transfer, it was once again brought to the sterile room, opened on a laminar flow clean bench and aseptically manipulated. Multiplication stage culture from approximately 50 test tubes was divided by conventional tissue culture techniques and transferred to 200 test tubes each containing 10 ml of growth stage medium. This medium was composed of half strength of MS macro nutrients, full strength MS micro nutrients, myo-inositol 100 mg/liter, glycine 2 mg/l, nicotinic acid 5 mg/l, IAA 2 mg/l, thiamine 10 mg/l, adenine sulphate 20 mg/l, sucrose 30 grams/liter, Difco Bacto-Agar 10 grams/liter and was adjusted to pH 5.7 before autoclaving. The test tubes were then sealed with Kimble PM caps and returned to the culture room. This growth stage culture developed into plantlets which were transferred to the greenhouse for horticultural tests.

The remaining multiplication stage culture (about 250 test tubes) was transferred to 12 flasks of liquid multiplication stage medium (this medium differed from the solid medium only in that it was without agar and that the pH before autoclaving was 5.1). The contents of about 20 test tubes (approx. 20 grams of plant tissue) was placed in each 500 ml flask which also contained 150 ml of multiplication stage medium. The flasks were sealed with sterile cotton plugs and placed on an orbital shaker at 125 RPM in the culture room under the same environmental conditions as previously noted. After about four weeks on a shaker, the medium was tested for sterility in the manner previously described using three separate index media. Two weeks after the medium samples were withdrawn, one of the multiplication stage culture flasks which was shown to be contaminated was discarded and the rest of the flasks brought to the homogenization procedure.

Homogenization and Dispensing Procedure

Prior to the homogenization procedure, all the equipment was autoclaved and arranged in the sterile room as previously described. The holding tank was charged with two liters of agar-based multiplication stage medium and the sterilization cycle begun. After the medium in the holding tank was cooled to 37° C. the tank was aseptically connected to the rest of the equipment, and the homogenization procedure begun. Two flasks of sterile multiplication stage culture and about 200 ml of distilled water were poured into the blender. The blender was sealed and run for 7 seconds at low speed. The inflow and outflow valves were then opened and the peristaltic pumps—which bring sterile water into the blender and pump dilute homogenate to the sieving apparatus—were started. The dilute homogenate entered the sieving apparatus. Large pieces of tissue were trapped by the coarse sieve (3,150 micron mesh opening), propagules (i.e. pieces of tissue capable of regenerating in a relatively short period of time) were held by the fine sieve. (500 micron mesh opening) and all debris passed to the container under the fine sieve. From here this waste solution was pumped to a carboy for disposal. When the blender was emptied of plant material the peristaltic pumps were stopped, the inflow and outflow valves shut, and the blender opened. The plant material trapped by the coarse sieve was reintroduced in to the blender along with the contents of two more flasks of multiplication stage culture and the above process repeated. Homogenization continued until eight flasks (which is approximately 640 grams of plant material) were processed. The propagules in the fine sieve were then washed, suspended in 2 liters of sterile distilled water, pumped to the holding tank and dispensed to 26

100 cm² culture vessels according to the procedure detailed earlier.

The filled vessels were sealed with parafilm and then transferred to the culture room with the same environmental conditions as described for the conventional tissue culture. After about six weeks in this culture room the multiplication stage culture was aseptically transferred to a liquid shake culture. This was accomplish, as described earlier, by aseptically removing the plants from each vessel, washing them free of agar and transferring them to a 500 ml flask containing 150 ml of multiplication stage liquid medium. These flasks were then sealed with sterile cotton plugs and placed on an orbital shaker at 125 RPM in the culture room. After three weeks in a liquid medium two flasks were discarded because of contamination, and 16 flasks were once again brought to the sterile room for separation and transfer to fresh medium by the homogenization process. Eight flasks were subcultured by being transferred again to a multiplication stage medium, once more this yielded 26 100 cm² culture vessels containing multiplication stage culture. The other eight flasks also yielded 26 100 cm² culture vessels but these were placed on a growth medium. After six to eight weeks in the culture room this culture produced about 100 plantlets per vessel which were then transferred to the greenhouse for horticultural tests. Thus, this subculture as well as the seven subsequent subcultures yielded 26 culture vessels for multiplication (of which 16 were used) and 26 culture vessels contained approximately 2,500 plantlets which were transferred to the greenhouse.

Verification of Phenotypic Stability

Plantlets of Philodendron Burgundy derived from the initial culture (200 plantlets) and eight subsequent subcultures (2,500 plantlets from each subculture) were transferred to the greenhouse, adapted to greenhouse conditions, grown for six months and examined for phenotypic stability. Plantlets received by the greenhouse were washed free of agar, separated into individual plants and dipped in a mixture of 96% rooting hormone (Stim Root No. 2(0,1% IBA) and 4% Teco 60 (60% 2-(4'-thiazol)benzinidazole). They were then planted in "Speedling" trays with 2.5 inch cells in a thoroughly moistened 2:1 mixture of peat and styrofoam beads. Next, they were placed on tables in the greenhouse which were covered by a polycarbonate tunnel designed to maintain humid environment around the plants. While on this table the plants received water by overhead mist for one minute each day. After three weeks under these conditions the plants were well rooted and the polycarbonate tunnel was gradually opened to slowly adapt the plants to the general greenhouse environment.

After several months in "Speedling" trays the plants were transferred to No. 12 pots and grown under standard greenhouse conditions for six months. During their growth the plants were evaluated for speed and habit of growth and shape and colour of foliage. It was found that none of the plants from any of the subcultures differed significantly from the commercially acceptable phenotype and consequently all plants were sold.

EXAMPLE 2

Tissue culture of Nephrolepis bostoniensis exaltata (Boston Fern) was initiated and subsequently subcultured and propagated for six generations using the process described above. Two hundred plantlets from the initial culture and 4000 plantlets from each subculture were transferred to the greenhouse and grown for approximately 4 months. Beginning with the sixth generation, unacceptable phenotypic variability was observed and subculturing discontinued.

Maintenance of Stock Plants

Explant tissue was derived from 250 one-year old Boston Fern mother plants. These plants had been maintained for at least six months under conditions which would facilitate obtaining non-contaminated explants. More particularly, these plants were grown in individual pots in a greenhouse with a relatively low humidity (approx. 70%) and a relatively high temperature (approx. 25° C.). These plants received water only at the base and were prophylactically sprayed with the fungicide Benlate (1 gm/liter) and Captan (2 g/l) once a week.

Initiation of 'In Vitro' Culture

Several days after the plants were sprayed with fungicides, 800 runner tips (3-4 cm long) were removed from the mother plants and brought to the laboratory. The explants were surface sterilized by immersion first in a 0.5% Sodium Hypochlorite solution for 20 minutes and then dipped in a 70% Ethanol solution. The explants were then brought to the sterile room, placed on a laminar flow clean bench and rinsed three times in sterile distilled water. The runner tips were then aseptically trimmed down to a section 1 cm in length and placed in test tubes, on 20 ml of initiation stage medium. This medium consisted of a modified Murashige and Skoog (1962) mixture of inorganic salts containing half the level of $NH_4NO_3$, $KNO_3$, $CaCl_2$, $2H_2O$, $Mg\ SO_4$, $7H_2O$, $KH_2PO_4$ and standard levels of the remaining inorganic constituents. Organic constituents included NAA (0.1 mg/liter) Kinetin (1 mg/liter), Myo-Inositol (500 mg/liter), sucrose (20 g/liter) Difco Bacto-Agar 10 grams/liter and the medium was adjusted to pH 5.7 before autoclaving. The test tubes were then sealed with Kimble PM (permeable membrane) caps and placed in the culture room, which was maintained at 26° C.±1 under 4000 lux cool white fluorescent illumination and a 16 hour photoperiod. The culture was inspected weekly and contaminated test tubes were removed and discarded.

Initiation of Multiplication Stage

After about 12 weeks in the culture room developed explants were returned to the sterile room for transfer. Of the original 800 explants approximately 350 had developed and were not visibly contaminated. These explants were aseptically trimmed, separated and placed in 600 test tubes with fresh multiplication stage medium, the composition of which differed from initiation stage medium only in that the hormone IAA (0.3 mg/liter) was substituted for NAA and Kinetine. The test tubes were then sealed and returned to the culture room.

After approximately six weeks the culture was again ready for transfer. Since the multiplication and growth stage media were identical, it was possible at this time to transfer plantlets from 200 test tubes directly to the greenhouse for horticultural tests. The remaining multiplication stage culture (approximately 400 test tubes) was brought to the sterile room, opened on a laminar flow clean bench and aseptically transferred to 12 flasks of liquid multiplication stage medium. (This medium differed from the previous multiplication stage medium only in that it was without agar and that the pH before autoclaving was 5.1). The contents of about 25 test tubes (approx. 20 g of plant tissue) was placed in each 500 ml flask which also contained 150 ml of multiplication stage medium. The flasks were sealed with sterile cotton plugs and placed on an orbital shaker at 125 RPM in the culture room under the same environmental conditions as previously noted.

After about 4 weeks on a shaker, the multiplication stage culture medium was tested for sterility in the manner previously described using three separate index media. Two weeks after the medium samples were withdrawn, one of the multiplication stage culture flasks which was shown to be contaminated was discarded and the rest of the flasks brought to the homogenization procedure.

Homogenization and Dispensing Procedure

Prior to the homogenization procedure, all the equipment was autoclaved and arranged in the sterile room as previously described. The holding tank was charged with two liters of agar-based multiplication stage medium and the sterilization cycle begun. After the medium in the holding tank was cooled to 37° C. the tank aseptically connected to the rest of the equipment, and the homogenization procedure begun. Two flasks of sterile multiplication stage culture and about 200 ml of distilled water were poured into the blender. The blender was sealed and run for 7 seconds at low speed. The inflow and outflow valves were then opened and the peristaltic pumps—which bring sterile water into the blender and pump dilute homogenate to the sieving apparatus—were started and the dilute homogenate entered the sieving apparatus. With ferns, there are no large pieces of tissue to be trapped by the coarse sieve so that all the plant material passed to the fine sieve. Pieces of tissue capable of regenerating were held by this sieve, while cell debris passed through it to the container below. From here waste solution was pumped to a carboy for disposal.

When the blender was emptied of plant material the peristaltic pumps were stopped, the inflow and outflow valves shut, and the blender opened. The contents of two more flasks of multiplication stage culture was introduced to the blender and the process repeated. Homogenization continued until eight flasks (approximately 640 grams of plant material) were processed. The plant material in the fine sieve was then washed, suspended in 2 liters of sterile distilled water, pumped to the holding tank and dispensed to 26 100 cm$^2$ culture vessels according to the procedure detailed earlier.

The filled vessels were sealed with parafilm and then transferred to the culture room with the same environmental conditions as described for the conventional tissue culture. After about six weeks in this culture room the multiplication stage culture was aseptically transferred to a liquid shake culture. This was accomplished, as described earlier, by aseptically removing the plants from each vessel, washing them free of agar and transferring them to a 500 ml flask containing 150 ml of multiplication stage medium. These flasks were then sealed with sterile cotton plugs and placed on an orbital shaker at 125 RPM in the culture room. After three weeks in a liquid medium three flasks were discarded because of contamination, and 16 flasks were once again brought to the sterile room for separation and transfer to fresh medium by the homogenization process. Sixteen flasks were subcultured by being transferred again to a multiplication stage medium. This yielded 52 100 cm$^2$ culture vessels containing plant material which could be used for either further multiplication or transfer to the greenhouse. After six to eight weeks in the culture room, 26 culture vessels, each containing approximately 150 plantlets, were transferred to the greenhouse for horticultural tests. The contents of sixteen culture vessels were transferred back again to liquid medium for further subculture and the rest of the vessels were discarded. Thus, this subculture as well as subsequent subcultures yielded 26 culture vessels for multiplication (of which 16 were used) and 26 culture vessels containing approximately 4,000 plantlets which were transferred to the greenhouse.

Verification of Phenotypic Stability

Plantlets of Boston Fern derived from the initial culture (200 plantlets) and subsequent subcultures (4,000 plantlets from each subculture) were transferred to the greenhouse, adapted to greenhouse conditions, grown for 4 months and examined for phenotypic stability. Plantlets received by the greenhouse were washed free of agar, separated into individual plants and dipped in a mixture of 96% rooting hormone (Stim Root No. 2 (0.1% IBA)) and 4% Teco 60 (60% 2 (4' thiazol) benzinidazole)). They were then planted in "Speedling" trays with 2.5 inch cells in a thoroughly moistened 2:1 mixture of peat and styrofoam beads. Next, they were placed on tables in the greenhouse which were covered by a polycarbonate tunnel designed to maintain humid environment around the plants. While on this table the plants received water by overhead mist for one minute each day. After two weeks under these conditions the plants were well rooted and the polycarbonate tunnel was gradually opened to allow the plants to slowly adapt to the general greenhouse environment.

After two months in "Speedling" trays, the plants were transferred to 4 inch pots and grown under standard greenhouse conditions for another 2 months. During their growth the plants were evaluated for speed and habit of growth and shape and colour of foliage. It was found that none of the plants from the first five subcultures differed significantly from the commercially acceptable phenotype and consequently all plants were sold. Beginning with the sixth subculture, plants began to show unacceptable deviations in foliage shape and growth habit. Consequently subculturing was discontinued.

As will be realized, the present process of at least partial automation of propagation by plant tissue culture is potentially applicable to any crop which can be propagated 'In Vitro'. This would include many foliage plants, ornamental plants, flower crops, woody plants and vegetable crops. Of course, the crops which are currently propagated commercially by tissue culture methods would be particularly suited to this process. These would primarily be ornamental crops such as ferns, Philodendron, Ficus, Bromeliaceae, etc., but would also include limited production of vegetable crops for special purposes such as disease-free Asparagus and parent lines of Broccoli, and also limited production of a few woody species. These crops are currently produced by labor intensive conventional tissue culture techniques which means that laboratory production cannot exceed 1000-2000 plants per day per person. The invention in its present form should be able to produce 7000 to 15,000 plants per day per person which provides a considerable saving to the propagator.

In addition to the reduction in cost of tissue culture for crops presently propagated 'In Vitro', the low unit cost of the process would make it applicable to crops for which commercial tissue culture propagation currently has no economic advantage. For example, use of the process for the propagation of ornamentals such as Saintpaulia or Streptocarpus would result in their tissue culture propagation being less expensive than their propagation by conventional greenhouse methods. Moreover, the process may make projects such as clonal propagation of forest trees and hydrid vegetable crops feasible, provided sufficient economies of scale can be made using the invention and that improvements in automation of transplanting plantlets are forthcoming.

The process will also have several applications in plant breeding. One application will be the propagation of seed-parents of commercial $F_1$ hybrid vegetables. The seed-parent lines may be homozygous but difficult to propagate by seed (e.g. genetic male sterility) or they may be heterozygous according to the method of Lawrence, Jr. et al U.S. Pat. No. 4,326,358. Another application to plant breeding is the use of the process for large scale 'In Vitro' selection at the whole plant level.

Reference will now be made in greater detail to the plant tissue culture vessel and to its use in the process that has been described.

For use in said process and other uses as well the present invention provides a plant tissue culture vessel provided with a substantially flat fine screening element elevated above the inner bottom surface of the vessel, said vessel being sterilizable, substantially sealable and adapted for growing plant tissue cultures supported on the surface of said screening element in optimal contact with culture medium filling said vessel to the level of said screening element, said screening element being sized to permit the passage of said culture medium therethrough while retaining said tissue culture on the surface thereof.

In one possible embodiment of the present invention said screening element is supported an projections provided on the inner side salls of said vessel, while in preferred embodiments of the invention, as described in greater detail hereinafter, said screening element is supported within said vessel on a pallet-like grid element positioned on the inner bottom surface of said vessel, said pallet being provided with apertures facilitating free flow of liquid within the areas defined by said grid.

Preferably said screening element has a mesh size of about 250 to 4,000 microns and a screening element having a mesh size of about 500 to about 700 microns is especially preferred.

In hydroponic and other similar seed sprouting systems such as described in U.S. Pat. Nos. 2,062,755; 4,057,930; 4,135,331; and 4,355,484 there are described different arrangements of seed and/or plant supporting screens, however these are provided in order to support the seed or plant over a water or liquid medium so that they won't drown therein and said patents do not teach or suggest the use of the presently claimed screening element in the non-analogous art of plant tissue culture propagation since in plant tissue culture propagation, the plant tissue culture propagules are usually embedded in the culture medium and the problem of drowning in liquid simply does not exist.

Thus despite the existence of the art of water culture growing of plants on supporting screens for over fifty years as described, e.g., in U.S. Pat. No. 2,062,755 heretofor no advantage was recognized for the use of a screening element in plant-tissue culture propagation. Furthermore, the screen support elements used in said hydroponic systems are several orders of magnitude larger than those used in the present invention and are not sized to permit the passage of culture medium therethrough while retaining tissue culture on the surface thereof as described and claimed herein.

Said vessel is preferably made of autoclavable material such as polycarbonate plastic or other similar material as described, e.g., in U.S. Pat. Nos. 4,224,765 and 4,358,908.

As already indicated the invention is primarily useful in the production of tissue culture derived plantlets by automated procedures. After the plant tissue is cut and/or divided in bulk, it must be mechanically transported to a culture vessel and planted in contact with a medium in that vessel in such a manner as to facilitate growth and development in the tissue. Now, this can simply be accomplished by suspending the plant tissue in a liquid and volumetrically dispensing this suspension to a culture vessel according to the present invention. .

When a mixture of plant tissue and medium is dispensed to the presently proposed vessel the medium passes through the screen while the plant tissue is held by the screen. When the mixture is added until the level of the medium reaches the level of the screen, the plant material lies on an even layer on top of a medium base. This is the optimal configuration for the growth and development of the tissue into plantlets.

Another advantage of the vessel of the present invention is to allow the bulk transfer of developing tissue culture to fresh liquid or solid medium. When an Agar based medium is used, the plant tissue loosely adheres to the screen, consequently the bulk transfer can be effected simply by moving the screen to a new vessel containing a liquid or solid medium base. Alternatively, if the tissue culture is resting on a liquid medium, then fresh medium can be added to the culture vessel after the spent medium is removed by aspiration.

A further advantage is to allow the bulk removal of developed plantlets for inexpensive packaging and shipping.

Yet another advantage is to allow for inexpensive 'in vitro' screening of whole plantlets for resistance to environmental stress. That is, plantlets grown on the screening element can be transferred in bulk to a medium which contains the agent to be selected against. Here simply, the liquid medium under the screening element can be changed and the agent to be selected against introduced with the new medium.

Referring now to the drawings in detail, there is seen an autoclavable polycarbonate vessel 25 fitted with a fine 600 micron mesh autoclavable nylon screen 26 one cm above the inner bottom surface 27 of the vessel. The screen forms a flat surface in the vessel covering its entire inside dimension so that very little plant material can flow around the screen. The screen rests on an autoclavable polycarbonate pallet-like grid element 28 designed to allow the screen to remain flat while the medium/plant tissue mixture is dispensed. The pallet 28 is also designed to establish an even distribution of medium throughout the vessel by permitting the medium to flow through apertures 29 in the lower portion of the walls of the pallet 28. After filling, the vessel is closed with an autoclavable polycarbonate cover 30 sized to tightly close said vessel 25.

In operative use, medium/plant tissue mixture is evenly dispensed on the surface of the screen 26. When the medium reaches the level of the screen-dispensing is terminated. The vessel is thus filled in such a manner that an even layer of plant tissue rests on/and in good contact with a medium base and the vessel is then sealed with its cover 30.

It will be evident to those skilled in the art that the invention is not limited to the details of the foregoing illustrative embodiments and examples and that the present invention may be embodied in other specific forms without departing from the essential attributes thereof, and it is, therefore, desired that the present embodiments and examples be considered in all respects as illustrative and not restrictive, reference being made to the appended claims, rather than to the foregoing description, and all changes which come with the meaning and range of equivalency of the claims are, therefore, intended to be embrced therein.

I claim:

1. A process of plant tissue culture propagation comprising the steps of:
   providing a mass of sterile meristematic tissue;
   dividing said mass into clusters;
   sizing said clusters to provide propagules of a predetermined size;
   washing said propagules to remove phytotoxic cell debris; and
   distributing the washed propagules on the surface of a culture medium;
   Wherein prior to the providing of said propagules said clusters are transported in bulk along a first enclosed predetermined flow path, wherein prior to said distributing the washed propagules are transported in bulk along a second enclosed predetermined flow path, and wherein the entire process is performed under aseptic conditions;
   wherein, prior to said distributing, the washed propagules are suspended in a liquid culture medium to define a propagule suspension, and wherein said distributing comprises the steps of (a) dispensing a predetermined volume of the propagule suspension into a vessel via screening means disposed therein and having a predetermined mesh size, (b) retaining propagules of the dispensed suspension on said screening means and (c) permitting said medium to pass through said screening means; and wherein said process further comprises the steps of:
   providing said medium in said vessel up to said screening means and in contact with the propagules retained thereon; and
   permitting development of said propagules retaining on said screening means;
   wherein said screening means is disposed in said vessel by supporting the screening means on a grid positioned on the inner bottom surface of the vessel, the grid being provided with apertures for facilitating free flow of culture medium therethrough.

2. A process of plant tissue culture propagation comprising the steps of:
   providing a mass of sterile meristematic tissue;
   dividing said mass into clusters;
   sizing said clusters to provide propagules of a predetermined size;
   washing said propagules to remove phytotoxic cell debris; and
   distributing the washed propagules on the surface of a culture medium;
   wherein prior to the providing of said propagules said clusters are transported in bulk along a first enclosed predetermined flow path, wherein prior to said distributing the washed propagules are transported in bulk along a second enclosed predetermined flow path, and wherein the entire process is performed under aseptic conditions;
   wherein, prior to said distributing, the washed propagules are suspended in a liquid culture medium to define a propagule suspension, and wherein said distributing comprises the steps of (a) dispensing a predetermined volume of the propagule suspension into a vessel via screening means disposed therein and having a predetermined mesh size, (b) retaining propagules of the dispensed suspension on said screening means and (c) permitting said medium to pass through said screening means; and wherein said process further comprises the steps of
   providing said medium in said vessel up to said screening means and in contact with the propagules retained thereon; and
   permitting development of said propagules retained on said screening means;
   wherein said screening means is disposed in said vessel by supporting the screening means on projections provided on inner sidewalls of said vessel.

3. A process of plant tissue culture propagation comprising the steps of:
   providing a mass of sterile meristematic tissue;
   dividing said mass into clusters;
   sizing said clusters to provide propagules of a predetermined size;
   washing said propagules to remove phytotoxic cell debris; and
   distributing the washed propagules on the surface of a culture medium;
   wherein prior to the providing of said propagules said clusters are transported in bulk along a first enclosed predetermined flow path, wherein prior to said distributing the washed propagules are transported in bulk along a second enclosed predetermined flow path, and wherein the entire process is performed under aseptic conditions;
   wherein, prior to said distributing, the washed propagules are suspended in a liquid culture medium to define a propagule suspension, and wherein said distributing comprises the steps of (a) dispensing a predetermined volume of the propagule suspension into a vessel via screening means disposed therein and having a predetermined mesh size, and (b) retaining propagules of the dispensed suspension on said screening means and (c) permitting said medium to pass through said screening means; and wherein said process further comprises the steps of
   providing said medium in said vessel up to said screening means and in contact with the propagules retained thereon; and
   permitting development of said propagules retained on said screening means;
   wherein said propagules of the dispensed suspension are retained on said screening means by providing said screening means with a mesh size of about 250 to 4000 microns.

4. A process of plant tissue culture propagation comprising the steps of:
providing a mass of sterile meristematic tissue;
dividing said mass into clusters;
sizing said clusters to provide propagules of a predetermined size;
washing said propagules to remove phytotoxic cell debris; and
distributing the washed propagules on the surface of a culture medium;
wherein prior to the providing of said propagules said clusters are transported in bulk along a first enclosed predetermined flow path, wherein prior to said distributing the washed propagules are transported in bulk along a second enclosed predetermined flow path, and wherein the entire process is performed under aseptic conditions;
wherein, prior to said distributing, the washed propagules are suspended in a liquid culture medium to define a propagule suspension, and wherein said distributing comprises the steps of (a) dispensing a predetermined volume of the propagules suspension into a vessel via screening means disposed therein and having a predetermined mesh size, (b) retaining propagules of the dispensed suspension on said screening means and (c) premitting said medium to pass through said screening means; and wherein said process further comprises the steps of
providing said medium in said vessel up to said screening means and in contact with the propagules retained thereon; and
permitting development of said propagules retained on said screening means;
wherein said propagules of the dispensed suspension are retained on said screening means by providing said screening means with a mesh size of about 500 to 700 microns.

5. A process of plant tissue culture propagation comprising the steps of:
providing a mass of sterile meristematic tissue;
dividing said mass into clusters;
sizing said clusters to provide propagules of a predetermined size;
washing said propagules to remove phytotoxic cell debris; and
distributing the washed propagules on the surface of a culture medium;
wherein prior to the providing of said propagules said clusters are transported in bulk along a first enclosed predetermined flow path, wherein prior to said distributing the washed propagules are transported in bulk along a second enclosed predetermined flow path, and wherein the entire process is performed under aseptic conditions;
wherein, prior to said distributing, the washed propagules are suspended in a liquid culture medium to define a propagule suspension, and wherein said distributing comprises the steps of (a) dispensing a predetermined volume of the propagule suspension into a vessel via screening means disposed therein and having a predetermined mesh size, (b) retaining propagules of the dispensed suspension on said screening means and (c) permitting said medium to pass through said screening means; and wherein said process further comprises the steps of
providing said medium in said vessel up to said screening means and in contact with the propagules retained thereon; and
permitting development of said propagules retained on said screening means;
wherein said vessel is provided with a cover that closes said vessel during development of said propagules retained on said screening means.

6. A process of plant tissue culture propagation comprising the steps of:
providing a mass of sterile meristematic tissue;
driving said mass into clusters;
sizing said clusters to provide propagules of a predetermined size;
washing said propagules to remove phytotoxic cell debris; and
distributing the washed propagules on the surface of a culture medium;
wherein prior to the providing of said propagules said clusters are transported in bulk along a first enclosed predetermined flow path, wherein prior to said distributing the washed propagules are transported in bulk along a second enclosed predetermined flow path, and wherein the entire process is performed under aseptic conditions;
wherein, prior to said distributing, the washed propagules are suspended in a liquid culture medium to define a propagule suspension, and wherein said distributing comprises the steps of (a) dispensing a predetermined volume of the propagule suspension into a vessel via screening means disposed therein and having a predetermined mesh size, (b) retaining propagules of the dispensed suspension on said screening means and (c) permitting said medium to pass through said screening means; and wherein said process further comprises the steps of
providing said medium in said vessel up to said screening means and in contact with the propagules retained thereon; and
permitting development of said propagules retained on said screening means;
wherein, after permitting development of said propagules retained on said screening means, said process further comprises the step of removing said medium from said vessel and replacing it with a fresh medium.

7. A process of plant tissue culture propagation comprising the steps of:
providing a mass of sterile meristematic tissue;
dividing said mass into clusters;
sizing said clusters to provide progagules of a predetermined size;
washing said propagules to remove phytotoxic cell debris; and
distributing the washed propagules on the surface of a culture medium;
wherein prior to the providing of said propagules said clusters are transported in bulk along a first enclosed predetermined flow path, wherein prior to said distributing the washed propagules are transported in bulk along a second enclosed predetermined flow path, and wherein the entire process is performed under aseptic conditions;
wherein, prior to said distributing, the washed propagules are suspended in a liquid culture medium to define a propagule suspension, and wherein said distributing comprises the steps of (a) dispensing a predetermined volume of the propagule suspension into a vessel via screening means disposed therein and having a predetermined mesh size, (b) retaining propagules of the dispensed suspension on said screening means and (c) permitting said medium to pass through said screening means; and wherein said process further comprises the steps of providing said medium in said vessel up to said screening means and in contact with the propagules retained thereon; and permitting development of said propagules retained on said screening means;

wherein, after permitting development of said propagules retained on said screening means, said process further comprises the steps of removing said screening means from said vessel, together with developing tissue culture thereon, and placing said screening means and said developing tissue culture in a new vessel containing a tissue culture medium.

* * * * *